United States Patent
Zhang et al.

(10) Patent No.: US 8,519,191 B2
(45) Date of Patent: Aug. 27, 2013

(54) SYNTHESIS METHOD OF 3-METHYLAMINO-1, 2-PROPANEDIOL

(75) Inventors: Zhongfa Zhang, Weifang (CN); Xueyang Guo, Weifang (CN); Hui Huang, Weifang (CN)

(73) Assignee: Weifang PBNS Chem. Industry Co., Ltd, Weifang, Shandong (CN)

( * ) Notice: Subject to any disclaimer, the term of this patent is extended or adjusted under 35 U.S.C. 154(b) by 0 days.

(21) Appl. No.: 13/142,716

(22) PCT Filed: Mar. 12, 2010

(86) PCT No.: PCT/CN2010/071007
§ 371 (c)(1),
(2), (4) Date: Sep. 13, 2011

(87) PCT Pub. No.: WO2011/075966
PCT Pub. Date: Jun. 30, 2011

(65) Prior Publication Data
US 2012/0277471 A1    Nov. 1, 2012

(30) Foreign Application Priority Data
Dec. 25, 2009    (CN) .......................... 2009 1 0256073

(51) Int. Cl.
*C07C 213/04*    (2006.01)
*C07C 213/02*    (2006.01)

(52) U.S. Cl.
USPC .......................................... 564/479; 564/483

(58) Field of Classification Search
None
See application file for complete search history.

(56) References Cited

PUBLICATIONS

Database CAPLUS on STN, Acc. No. 1999:660378, Luo et al., CN 1132739 A (Oct. 9, 1996) (abstract).*

* cited by examiner

*Primary Examiner* — Brian J Davis
(74) *Attorney, Agent, or Firm* — Andrus, Sceales, Starke & Sawall, LLP

(57) ABSTRACT

A synthesis method of 3-methylamino-1,2-propanediol is disclosed in the invention, and it includes the following steps: (a) adding glycerin chlorohydrin, aqueous monomethylamine solution and an amination catalyst, namely NaOH solution and $NaHCO_3$, into a reactor, mixing the material sufficiently, and allowing amination reaction to proceed in two temperature stages; (b) removing monomethylamine and water from the amination solution after the amination reaction is completed, filtering out the solid resultant, and feeding the filtrate into a still; (c) distilling under reduced pressure to obtain 3-methylamino-1,2-propanediol, wherein the vacuum for distillation under reduced pressure is equal to or greater than 0.099 MPa and the temperature is 130-160° C.

8 Claims, No Drawings

SYNTHESIS METHOD OF 3-METHYLAMINO-1, 2-PROPANEDIOL

CROSS-REFERENCE TO RELATED APPLICATIONS

This application is the U.S. national stage application of International Application PCT/CN2010/071007, filed Mar. 12, 2010, which application is incorporated herein by reference. The International Application claims priority of Chinese Application No. 200910256073.6, filed Dec. 25, 2009, which application is incorporated herein by reference.

TECHNICAL FIELD

The invention relates to the field of chemical synthesis, and more particularly to a synthesis method of 3-methylamino-1, 2-propanediol.

BACKGROUND OF THE INVENTION

The contrast media used in radiological examination of medical technology include hyperosmolar ionic and hypoosmolar nonionic contrast media, wherein hyperosmolar ionic contrast medium has the disadvantages of leading to increased intravascular fluid, angiectasis, rising pulmonary venous pressure, vascular endothelial injury and large neurotoxicity, and rendering toxic and side effects in use, whereas nonionic contrast medium, applicable for blood vessel, nervous system, contrast enhanced CT scanning and the like, has the advantages of relatively low osmosis, low viscosity, and low toxicity, etc., alleviating toxic and side effects greatly. Among others, iopromide is a novel hypo-osmolar nonionic contrast medium, which has lower osmosis than ordinary ionic contrast medium, similar osmotic pressure to that of blood plasma, modest viscosity favorable for injection and less toxicity than ionic contrast medium, and may be used in myelography, more safely.

3-methylamino-1,2-propanediol is an important material for producing iopromide as a hypo-osmolar nonionic contrast medium, and its content has a direct influence on the quality, the content of impurities, as well as the clinical effect of the final product iopromide, particularly on the occurrence of adverse reaction, etc.. If the content of impurities in 3-methylamino-1,2-propanediol is high, the synthesized iopromide in use will result in the following reactions: mild nausea, emesis, dizziness, acute emesis, chilly feeling, generalized urticaria, facial or laryngeal edema, bronchospasm, dyspnea-stethalgia, celialgia, headache or limb convulsion, etc.. In severe cases, prostration, unconsciousness, pneumonedema, heart arrest or ventricular fibrillation, acute arrhythmia or myocardial infarct, or even death may be incurred. In view of the aforementioned reasons, Schering Co. of Germany has been extremely critical of the quality of 3-methylamino-1,2-propanediol since 1985 when iopromide was officially put into market, and only a few countries can produce the product satisfying its quality demand.

The processes for preparing 3-methylamino-1,2-propanediol may be categorized on the basis of starting material into epichlorohydrin process, glycerin chlorohydrin process, glycide process and glyceraldehyde process, wherein the aminating agent includes aqueous monomethylamine solution or gaseous monomethylamine used directly; it may be categorized on the basis of operational pressure into low pressure process, high pressure process, etc.; it may be categorized on the basis of production process into batch process and continuous process. Both epichlorohydrin and glycerin chlorohydrin processes take the route involving glycerin chlorohydrin, and they only differ in cost. Glycide and glyceraldehyde processes have high production cost, poor economic benefit and low purity of product. Therefore, glycerin chlorohydrin process is the most commonly used production process at present, wherein glycerin chlorohydrin and aqueous monomethylamine solution, as the starting materials at a feeding ratio of 1:2.9-3.9 by weight, are subjected to amination reaction under a pressure of 0.3-0.4 MPa, and then an aliphatic alcohol such as methanol or ethanol is used as a solvent to dilute the viscous solution to filter out monomethylamine chloride, followed by purification by means of distillation to obtain the product 3-methylamino-1,2-propanediol. The existing production of 3-methylamino- 1,2-propanediol mainly has the following disadvantages: (1) excessive feeding ratio of monomethylamine to glycerin chlorohydrin, bringing difficulty for recovery of monomethylamine, and increasing energy consumption; (2) low purity of the product and high content of impurities; (3) low conversion of glycerin chlorohydrin; (4) the requirement of using an aliphatic alcohol such as methanol or ethanol, as a solvent, to dilute the viscous solution and to filter out monomethylamine chloride, which adds operational steps; and (5) long production cycle.

SUMMARY OF THE INVENTION

The technical problem to be solved by the present invention is to provide a method for synthesizing 3-methylamino-1,2-propanediol, which can enhance the purity of 3-methylamino-1,2-propanediol in the product, reduce the content of impurities, and enable the product meet the demand for high quality of synthesized iopromide.

The technical solution according to the present invention for solving the aforementioned technical problem is provided as follows.

A synthesis method of 3-methylamino-1, 2-propanediol includes the following steps:

(1) amination reaction: adding glycerin chlorohydrin, aqueous monomethylamine solution and an amination catalyst, namely NaOH solution and $NaHCO_3$, into a reactor, stirring to mix the material sufficiently, and allowing the amination reaction to proceed in two temperature stages;

(2) treatment of amination solution: removing monomethylamine and water from the amination solution after the amination reaction is completed, filtering out solid resultant, and feeding filtrate into a still;

(3) purification by distillation: heating the material in the still, and distilling under reduced pressure to obtain the product 3-methylamino-1,2-propanediol, wherein the vacuum for distillation under reduced pressure is equal to or greater than 0.099 MPa and the temperature is 130-160° C.

The weight ratio of the glycerin chlorohydrin, the aqueous monomethylamine solution, the $NaHCO_3$ and the NaOH solution is 1:1.97-2.3:0.38-0.48:0.33-0.41, wherein the weight percentage of the NaOH solution is 40 wt %, and the weight percentage of the aqueous monomethylamine solution is 40 wt %.

The amination reaction in two temperature stages is carried out at 40-50° C. for 60-80 minutes, and then the material is heated to 55-65° C. to allow the reaction to continue for 100-150 minutes, wherein the reaction pressure is equal to or less than 0.15 MPa.

The temperature of the material rises in 10±2 minutes.

After the amination reaction is completed, the monomethylamine gas in the reactor is recovered first of all; and then the amination solution is fed into the still for recovery of the unreacted monomethylamine in the liquid phase by distillation, wherein the recovery of monomethylamine by distillation is carried out first under atmospheric pressure and then under vacuum when the temperature of the material in the still is 110-120° C.

After recovery of the monomethylamine by distillation and removal of moisture, the temperature of the material in the still is decreased to 50-70° C., and the solid resultant is filtered out. The solid sodium chloride filtered out is collected for collective disposal.

Before purification by distillation in the step (3), distillation is carried out to recover front cut fraction, wherein the recovery of the front cut fraction by distillation is carried out under vacuum at the gas-phase temperature of 60-100° C. Before recovery of the front cut fraction, condensed liquid is recovered when the gas-phase temperature is lower than 60° C. to prepare 40 % NaOH solution. The recovered front cut fraction is made full use by combining with next batch of distilland. The main components of the front cut fraction are unreacted glycerin chlorohydrin from the starting material, a small amount of product 3-methylamino-1,2-propanediol and a small amount of hydroxyl compounds. When the gas-phase temperature exceeds 100° C. and tends to rise further, the material in the still is cooled to 80-90° C., and distillation under reduced pressure is set off.

Vacuum scraper film evaporation is used as the distillation method for distilling the material in the still under reduced pressure in step (3), wherein the vacuum scraper film evaporation is the distillation under vacuum by distributing the liquid material under high-speed rotation into uniform film to evaporate quickly.

By taking the aforementioned technical solution, the following beneficial effects are achieved according to the invention:

1. Because of the introduction of NaOH solution and $NaHCO_3$ in the amination reaction as aminating catalysts in the present invention, the reaction is catalyzed and the conversion of glycerin chlorohydrin is thus increased. It may be analyzed specifically as follows.

(1) The reaction system is made stronger alkaline, facilitating rapid substitution of $CH_3NH$— group for —Cl group in glycerin chlorohydrin molecule, so that the amination reaction time is reduced.

(2) Relatively higher concentration of $CH_3NH_2$ is ensured in the reaction system, which facilitates accelerating the reaction and reducing the reaction time. In the case that NaOH and $NaHCO_3$ are not added as the catalysts, HCl resulting from removal of Cl from glycerin chlorohydrin reacts with $CH_3NH_2$ in the system to form $CH_3NH_3Cl$. This inevitably consumes considerable amount of $CH_3NH_2$, which reduces the content of $CH_3NH_2$ in the system. Whereas after NaOH and $NaHCO_3$ are added, the resulted HCl reacts with NaOH and $NaHCO_3$ to form NaCl. Even if $CH_3NH_3Cl$ is formed in the system, NaOH and $NaHCO_3$ will further react with $CH_3NH_3Cl$ to form NaCl and $CH_3NH_2$ due to the relatively strong alkalinity of the reaction system. Thus, relatively high concentration of $CH_3NH_2$ is maintained in the system.

(3) The feeding ratio of monomethylamine to glycerin chlorohydrin may be reduced without affecting reaction rate and product quality.

(4) Conversion of glycerin chlorohydrin is increased.

(5) The pressure of amination reaction is reduced. Specifically, the operational pressure is lowered from 0.3-0.4 MPa in prior art to less than 0.15 MPa. Therefore, the production is safer, and the requirements for facility material, wall thickness, fasteners, processing and the like are decreased significantly.

2. Since HCl produced in the amination reaction is mostly converted to NaCl rather than $CH_3NH_3Cl$ in the system, in contrast to prior art, the operational steps including the step of using aliphatic alcohol as required to dissolve and dilute the material in order to filter out $CH_3NH_3Cl$ due to the viscous state of the material in the later stage of removing monomethylamine and water, the step of evaporating the aliphatic alcohol, and the like are left out. By appropriate adjustment of the production process, the salt may be filtered out while it is still hot once the amination solution is deaminated and dewatered to a certain extent. Thus, the production operation is made easier. Not only the unit operating cycle is shortened, but also the production cost and energy consumption are relatively reduced.

3. Since the product 3-methylamino-1,2-propanediol is distilled by way of vacuum scraper film according to the invention, the heating time for separation and purification of the product is reduced greatly, and thus the components of the product hardly decompose. Therefore, the product quality is improved significantly, and the content of 3-methylamino-1,2-propanediol in the product is increased to above 99.5% (GC). The product thus produced is a liquid that is totally colorless and transparent. Furthermore, compared with prior art, the energy consumption of the production is reduced remarkably. Specifically, power consumption is reduced by 20%, and coal consumption is reduced by 30%.

4. Monomethylamine, condensed water and front cut fraction distilled out from the amination solution according to the invention are all recycled, which avoids volatilization and waste of the production starting material. Therefore, the availability of the starting material is increased. The production is achieved in a hermetic and clean environment, and the operational conditions for the production are improved notably.

5. The product synthesized according to the invention, a liquid appearing colorless and transparent, has increased purity of above 99.5% (GC) and decreased impurities. Therefore, this product exactly meets the quality demand for synthesis of iopromide as a hypo-osmolar nonionic contrast medium.

DETAILED DESCRIPTION OF THE EMBODIMENTS

The invention will be further illustrated with reference to the following specific embodiments.

Embodiment 1

1. Amination Reaction: 100 kg $NaHCO_3$, 510 kg aqueous monomethylamine solution with a concentration of 40 wt %, 250 kg glycerin chlorohydrin and 90 kg 40 wt % NaOH solution were added to a 1000 L reactor sequentially, and then stirred for one hour. The reactants were heated to allow the reaction to proceed at 42° C. for 80 minutes. Then the temperature was increased to 60° C. in 10 minutes, and the reaction was allowed to proceed at 60° C. for 120 minutes. The reaction pressure was 0.12 MPa.

2. Treatment of Amination Solution: The purge value of the reactor was switched on to discharge gaseous monomethylamine in the reactor to a kettle for absorbing monomethylamine until there was no pressure in the reactor, and then the amination solution was transferred to a 1000 L still for recovery of monomethylamine by distillation. The material in the still was heated. When the gas-phase temperature reached 101° C., a jet vacuum pump was started to evacuate the still. Heating was continued until the temperature of the material in the reactor reached 115° C. Then heating was stopped and evacuation was continued. After recovery of monomethylamine was completed, the temperature of the material was decreased to 60° C., and the material in the still was pressed into a filter press using compressed air to filter out the solid material. The solid material that was filtered out was collected for collective disposal, and the filtrate was fed into a 500 L still.

3. Purification by Distillation: The jet vacuum pump was started, and the filtrate in the still was heated. The condensed liquid recovered before the gas-phase temperature reached 60° C. was used to prepare 40 wt % NaOH solution, and the liquid condensed between 60° C. and 100° C. was recovered as front cut fraction which was added to next batch of distilland for full use. When the gas-phase temperature exceeded 100° C. and tended to rise further, the still was cooled to 80° C. A vacuum group was turned on to keep the vacuum in the scraper film evaporator above 0.099 MPa. When the temperature was 140° C., the discharge valve at the bottom of the still was switched on to feed the scraper film evaporator at a feed rate of 0.1 m³/h. Qualified product 3-methylamino-1,2-propanediol was distilled out.

Table 1 shows the quality index of 3-methylamino-1,2-propanediol synthesized according to the aforementioned method.

TABLE 1

| No. | Test Index | Analysis Method | Test Results |
|---|---|---|---|
| 1 | Appearance | Eye inspection | Colorless and transparent liquid |
| 2 | Purity (GC) (%) | Gas chromatography | 99.56 |
| 3 | Cut fraction content before the principal peak (GC) (%) | Gas chromatography | 0.12 |
| 4 | Cut fraction content after the principal peak (GC) (%) | Gas chromatography | 0.32 |
| 5 | Moisture content (wt %) | Karl Fisher method | 0.93 |

Embodiment 2

1. Amination Reaction: 210 kg NaHCO₃, 1050 kg aqueous monomethylamine solution with a concentration of 40 wt %, 500 kg glycerin chlorohydrin and 183 g 40 wt % NaOH solution were added to a 2000 L reactor sequentially, and then stirred for 1.5 hours. The reactants were heated to allow the reaction to proceed at 45° C. for 70 minutes. Then the temperature was raised to 65° C. in 10 minutes, and the reaction was allowed to proceed at 65° C. for 100 minutes. The reaction pressure was 0.15 MPa.

2. Treatment of Amination Solution: The purge value of the reactor was switched on to discharge gaseous monomethylamine in the reactor to a kettle for absorbing monomethylamine until there was no pressure in the reactor, and then the amination solution was transferred to a 2000 L still for recovery of monomethylamine by distillation. The material in the still was heated. When the gas-phase temperature reached 101° C., a jet vacuum pump was started to evacuate the still. Heating was continued until the temperature of the material in the reactor reached 120° C. Then heating was stopped and evacuation was continued. After recovery of monomethylamine was completed, the temperature of the material in the still was decreased to 70° C., and the material was pressed into a filter press using compressed air to filter out the solid material. The solid material that was filtered out was collected for collective disposal, and the filtrate was fed into a 500 L still.

3. Purification by Distillation: The jet vacuum pump was started, and the filtrate in the still was heated. The condensed liquid recovered before the gas-phase temperature reached 60° C. was used to prepare 40 wt % NaOH solution, and the liquid condensed between 60° C. and 100° C. was recovered as front cut fraction which was added to next batch of distilland for full use. When the gas-phase temperature exceeded 100° C. and tended to rise further, the still was cooled to 80° C. A vacuum group was turned on to keep the vacuum in the scraper film evaporator above 0.099 MPa. When the temperature was 145° C., the discharge valve at the bottom of the still was switched on to feed the scraper film evaporator at a feed rate of 0.15 m³/h. Qualified product 3-methylamino-1,2-propanediol was distilled out.

Table 2 shows the quality index of 3-methylamino-1,2-propanediol synthesized according to the aforementioned method.

TABLE 2

| No. | Test Index | Analysis Method | Test Results |
|---|---|---|---|
| 1 | Appearance | Eye inspection | Colorless and transparent liquid |
| 2 | Purity (GC) (%) | Gas chromatography | 99.61 |
| 3 | Cut fraction content before the principal peak (GC) (%) | Gas chromatography | 0.14 |
| 4 | Cut fraction content after the principal peak (GC) (%) | Gas chromatography | 0.25 |
| 5 | Moisture content (wt %) | Karl Fisher method | 1.07 |

Embodiment 3

1. Amination Reaction: 200 kg NaHCO₃, 1000 kg aqueous monomethylamine solution with a concentration of 40 wt %, 475 kg glycerin chlorohydrin and 175 g 40 wt % NaOH solution were added to a 2000 L reactor sequentially, and then stirred for 1.5 hours. The reactants were heated to allow the reaction to proceed at 50° C. for 60 minutes. Then the temperature was raised to 65° C. in 10 minutes, and the reaction was allowed to proceed at 65° C. for 100 minutes. The reaction pressure was 0.15 MPa.

2. Treatment of Amination Solution: The purge value of the reactor was switched on to discharge gaseous monomethylamine in the reactor to a kettle for absorbing monomethylamine until there was no pressure in the reactor, and then the amination solution was transferred to a 2000 L still for recovery of monomethylamine by distillation. The material in the still was heated. When the gas-phase temperature reached 101° C., a jet vacuum pump was started to evacuate the still. Heating was continued until the temperature of the material in the reactor reached 115° C. Then heating was stopped and evacuation was continued. After recovery of monomethylamine was completed, the temperature of the material was decreased to 80° C., and the material in the still was pressed into a filter press using compressed air to filter out the solid material. The solid material that was filtered out was collected for collective disposal, and the filtrate was fed into a 1000 L still.

3. Purification by Distillation: The jet vacuum pump was started, and the filtrate in the still was heated. The condensed liquid recovered before the gas-phase temperature reached 60° C. was used to prepare 40 wt % NaOH solution, and the liquid condensed between 60° C. and 100° C. was recovered as front cut fraction which was added to next batch of distilland for full use. When the gas-phase temperature exceeded 100° C. and tended to rise further, the still was cooled to 80° C. A vacuum group was turned on to keep the vacuum in the scraper film evaporator above 0.099 MPa. When the temperature was 150° C., the discharge valve at the bottom of the still was switched on to feed the scraper film evaporator at a feed rate of 0.15 m³/h. Qualified product 3-methylamino-1,2-propanediol was distilled out.

Table 3 shows the quality index of 3-methylamino-1,2-propanediol synthesized according to the aforementioned method.

TABLE 3

| No. | Test Index | Analysis Method | Test Results |
|---|---|---|---|
| 1 | Appearance | Eye inspection | Colorless and transparent liquid |
| 2 | Purity (GC) (%) | Gas chromatography | 99.65 |
| 3 | Cut fraction content before the principal peak (GC) (%) | Gas chromatography | 0.09 |
| 4 | Cut fraction content after the principal peak (GC) (%) | Gas chromatography | 0.26 |
| 5 | Moisture content (wt %) | Karl Fisher method | 0.84 |

Industrial Practicability

1. Because of the introduction of NaOH solution and NaHCO$_3$ in the amination reaction according to the invention as aminating catalysts, (1) the reaction system is made stronger alkaline, facilitating rapid substitution of CH$_3$NH— group for —Cl group in glycerin chlorohydrin molecule, so that the amination reaction time is reduced; (2) relatively higher concentration of CH$_3$NH$_2$ is ensured in the reaction system, which facilitates accelerating the reaction and reducing the reaction time; (3) the feeding ratio of monomethylamine to glycerin chlorohydrin may be reduced without affecting reaction rate and product quality; (4) conversion of glycerin chlorohydrin is increased; and (5) the pressure of amination reaction is reduced, wherein the operational pressure is decreased from 0.3-0.4 MPa in prior art to less than 0.15 MPa, so that the production is safer, and the requirements for facility material, wall thickness, fasteners, processing and the like are lowered substantially.

2. Since HCl produced in the amination reaction is mostly converted to NaCl rather than CH$_3$NH$_3$Cl in the system, in contrast to prior art, the operational steps including the step of using aliphatic alcohol as required to dissolve and dilute the material in order to filter out CH$_3$NH$_3$Cl due to the viscous state of the material in the later stage of removing monomethylamine and water, the step of evaporating the aliphatic alcohol, and the like are left out. By appropriate adjustment of the production process, the salt may be filtered out while it is still hot once the amination solution is deaminated and dewatered to a certain extent. Thus, the production operation is made easier. Not only the unit operating cycle is shortened, but also the production cost and energy consumption are reduced.

3. Since the product 3-methylamino-1,2-propanediol is distilled by way of the vacuum scraper film according to the invention, the heating time for separation and purification of the product is reduced greatly, and thus the components of the product hardly decompose. Thus, the product quality is improved significantly, and the content of 3-methylamino-1,2-propanediol in the product is increased to above 99.5% (GC). The product thus produced is a liquid that is totally colorless and transparent. Furthermore, compared with prior art, the energy consumption of the production is reduced remarkably. Specifically, power consumption is reduced by 20%, and coal consumption is reduced by 30%.

4. Condensed water, monomethylamine and front cut fraction distilled out from the amination solution according to the invention are all recycled, which avoids volatilization and waste of the production starting material. Therefore, the availability of the starting material is increased. The production is achieved in a hermetic and clean environment, and the operational conditions for the production are improved notably.

5. The product synthesized according to the invention, a liquid appearing colorless and transparent, has increased purity of above 99.5% (GC) and decreased impurities. Therefore, this product exactly meets the quality demand for synthesis of iopromide as a hypo-osmolar nonionic contrast medium.

The invention claimed is:

1. A synthesis method of 3-methylamino-1,2-propanediol, comprising the following steps:
   (a) adding glycerin chlorohydrin, an aqueous monomethylamine solution, and an NaOH solution and NaHCO$_3$, into a reactor, stirring to mix the material, and allowing an amination reaction to proceed in two temperature stages;
   (b) treating an amination solution from the amination reation by removing monomethylamine and water from the amination solution after the amination reaction is completed, filtering out solid resultant, and feeding filtrate into a still;
   (c) heating the material in the still, and distilling under reduced pressure to obtain the product 3-methylamino-1,2-propanediol, wherein the vacuum for distillation under reduced pressure is equal to or greater than 0.099MPa and the temperature is 130-160° C.

2. The synthesis method of 3-methylamino-1,2-propanediol according to claim 1, wherein the weight ratio of the glycerin chlorohydrin, the aqueous monomethylamine solution, the NaHCO$_3$ and the NaOH solution is 1:1.97-2.3:0.38-0.48:0.33-0.41, wherein the weight percentage of the NaOH solution is 40wt %, and the weight percentage of the aqueous monomethylamine solution is 40w %.

3. The synthesis method of 3-methylamino-1,2-propanediol according to claim 1, wherein the amination reaction proceeded in the two stages is carried out at 40-50° C. for 60-80 minutes, and then the material is heated to 55-65° C. to allow the reaction to continue for additional 100-150 minutes.

4. The synthesis method of 3-methylamino-1,2-propanediol according to claim 3, wherein the temperature of the material rises in 10±2 minutes.

5. The synthesis method of 3-methylamino-1,2-propanediol according to claim 4, wherein after the amination reaction is completed, the monomethylamine gas in the reactor is recovered first of all; and then the amination solution is fed into the still for recovery of unreacted monomethylamine by distillation, wherein the recovery of the monomethylamine by distillation is carried out first under atmospheric pressure and then under vacuum when the temperature of the material in the still is 110-120° C.

6. The synthesis method of 3-methylamino-1,2-propanediol according to claim 5, wherein after recovery of the monomethylamine by distillation and removal of moisture, the temperature of the material in the still is decreased to 50-70° C. and the solid resultant is filtered out.

7. The synthesis method of 3-methylamino-1,2-propanediol according to claim 5, wherein before purification of the filtrate by distillation in the step (c), distillation is carried out to recover front cut fraction of the material in the still, wherein recovery of the front cut fraction by distillation is effected under vacuum at the gas-phase temperature of 60-100° C.

8. The synthesis method of 3-methylamino-1,2-propanediol according to claim 5, characterized in that vacuum scraper film evaporation is used as a distillation method for distilling the material in the still under reduced pressure in the step (c), wherein vacuum scraper film evaporation is distillation under vacuum by distributing the liquid material under high-speed rotation into a uniform film.

* * * * *

UNITED STATES PATENT AND TRADEMARK OFFICE
CERTIFICATE OF CORRECTION

PATENT NO. : 8,519,191 B2
APPLICATION NO. : 13/142716
DATED : August 27, 2013
INVENTOR(S) : Zhongfa Zhang et al.

It is certified that error appears in the above-identified patent and that said Letters Patent is hereby corrected as shown below:

The Assignee on the Title Page of the patent should appear as follows:

-- (73) Assignee: Weifang Xingxin Technical Services Ltd., Weifang City, Shandong Province (CN) --.

Signed and Sealed this
Fourth Day of February, 2014

Michelle K. Lee
*Deputy Director of the United States Patent and Trademark Office*